United States Patent [19]
Hirai et al.

[11] Patent Number: 5,591,406
[45] Date of Patent: Jan. 7, 1997

[54] AUTOMATIC EXHAUST GAS ANALYZER FOR AN INTERNAL COMBUSTION ENGINE

[75] Inventors: Kenji Hirai, Kameoka; Akira Aono; Shinya Tsuneda, both of Kyoto; Hirokazu Matsumoto, Otsu; Yuji Yamashita, Suita; Hisayoshi Tanaka, Kyoto; Takanori Shiina; Haruko Kaburagi, both of Utsunomiya, all of Japan

[73] Assignees: Shimadzu Corporation, Kyoto; Honda Giken Kogyo Kabushiki Kaisha, Tokyo, both of Japan

[21] Appl. No.: 527,434

[22] Filed: Sep. 13, 1995

Related U.S. Application Data

[63] Continuation of Ser. No. 290,286, Aug. 15, 1994, abandoned.

[30] Foreign Application Priority Data

Sep. 17, 1993 [JP] Japan .................................. 5-254887

[51] Int. Cl.⁶ ........................ G01N 31/12; G01N 30/02; G05D 9/00
[52] U.S. Cl. .................... 422/80; 422/89; 422/93; 422/94; 422/108; 73/23.22; 73/23.26; 73/23.41; 73/23.42
[58] Field of Search .................. 422/78, 80, 89, 422/93, 94, 107, 108; 374/36, 497; 73/23.22, 23.26, 23.41, 23.42

[56] References Cited

U.S. PATENT DOCUMENTS

| | | |
|---|---|---|
| 3,753,656 | 8/1973 | Matson et al. .................... 422/89 |
| 3,864,964 | 2/1975 | Voelz ................................ 73/116 |
| 3,923,460 | 12/1975 | Parrott et al. .................... 422/78 |
| 3,938,377 | 2/1976 | Converse, III et al. .......... 73/117 |
| 3,973,848 | 8/1976 | Jowett et al. .................... 356/51 |
| 3,998,095 | 12/1976 | Tinkham et al. ................. 73/117 |
| 4,951,503 | 8/1990 | Fini .................................. 73/23.1 |
| 5,019,517 | 5/1991 | Coulson .......................... 436/753 |
| 5,152,176 | 10/1992 | Bryselbout et al. ............. 73/23.4 |
| 5,279,146 | 1/1994 | Asano et al. .................... 73/28.04 |
| 5,357,791 | 10/1994 | Gee et al. ....................... 73/118.1 |

*Primary Examiner*—Nina Bhat
*Attorney, Agent, or Firm*—Oliff & Berridge

[57] ABSTRACT

An automatic exhaust gas analyzer for analyzing an exhaust gas of an internal combustion engine. The analyzer includes: a) plural analyzing units; b) two independent gas lines provided in each of the plural analyzing units; c) a gas-chromatographic column provided in each of the gas lines; d) a gas-chromatographic detector connected with the column in each of the gas lines; and e) a signal communication network interconnecting the gas-chromatographic detectors. Exhaust gas and the background gas are sampled at each stage of a predetermined run cycle, and are provided immediately to the two independent gas lines of the plurality of analyzing units respectively. Then the exhaust gas and background gas are analyzed in parallel in each of the plurality of analyzing units, which facilitates equalizing the measurement conditions of the two gases and the background correction of the measurement results of the exhaust gas can be made at high precision.

5 Claims, 5 Drawing Sheets

LA-4

AUTOMATIC EXHAUST GAS ANALYZER FOR AN INTERNAL COMBUSTION ENGINE

This is a continuation of application Ser. No. 08/290,286 filed Aug. 15, 1994, now abandoned.

The present invention relates to an apparatus for automatically analyzing the exhaust gas of the internal combustion engine of an automobile or other powered machines.

BACKGROUND OF THE INVENTION

In various regulations to the exhaust gas of automobiles, it is required to sample the exhaust gas when an automobile is running (on a chassis dynamometer) according to a predetermined run cycle. The run cycle is determined adequately regarding various actual running conditions of automobiles, and generally it includes a cold start, an idling and an acceleration.

In order to calculate various exhaust gas component parameters such as NMOG value, RAF value, etc., it is necessary to collect over one hundred kinds of data and to input the data into a predetermined calculating program. In this case, expertise for such kinds of data is necessary and the data input requires a lot of time with possible input errors.

Regulations to the exhaust gas of automobiles have been tightened year after year. Conventionally, exhaust gas of a sample automobile is sampled and stored in a predetermined run cycle and the stored gas is measured afterwards. Recently, the regulation has been changed to sample and measure the exhaust gas at each stage of the run cycle and the measured values should clear criteria values at each stage. For example, the exhaust gas regulation LA-4 of California State requires that the measured values of exhaust gas sampled at a cold start stage (CT), a steady run stage (CS) and a hot start stage (HT), as shown in FIG. 7, must clear the criteria values set for each stage. Thus the exhaust gas of the sample automobile running on a chassis dynamometer according to the pattern of FIG. 7 should be sampled at several preset time points.

Since the exhaust gas analysis needs high sensitivity and high precision, a gas chromatograph is used. In order to enhance the sensitivity of the measurement, the sampled gas should be concentrated before it is measured. It takes therefore nearly one hour to finish the measurements for the exhaust gas analysis. In many regulations on exhaust gas measurements, the ambient air (also called background gas) should be sampled at the same time as the exhaust gas. Thus it takes six hours in total to analyze the two kinds of gas (i.e., the exhaust gas and the background gas) sampled at the three stages of the LA-4 run cycle.

An important problem here is that the exhaust gas includes unstable components which may decompose when the sampled exhaust gas is left for a long time. The conventional measuring method described above requires a long time and cannot give adequate measurement results.

SUMMARY OF THE INVENTION

The present invention is thus proposed as the solution to the above problem and the automatic exhaust gas analyzer according to the present invention includes:

a) plural analyzing units;

b) two independent gas lines provided in each of the plural analyzing units;

c) a gas-chromatographic column provided in each of the gas lines;

d) a gas-chromatographic detector connected with the column in each of the gas lines; and e) a signal communication network interconnecting the gas-chromatographic detectors.

Exhaust gas and the background gas are sampled at each stage of a predetermined run cycle, and are provided immediately to the two independent gas lines of the plurality of analyzing units respectively. Then the exhaust gas and the background gas are analyzed in parallel in each of the plurality of analyzing units, which facilitates equalizing the measurement conditions of the two gases and the background correction of the measurement results of the exhaust gas can be made at high precision. Even if the gas samplings are performed with rather short intervals, the analysis of the later sampled gases can be started just after they are sampled without waiting for the finish of the analysis of the former sampled gases because plural analyzing units are provided in the automatic exhaust gas analyzer of the present invention. This shortens the overall measurement time length and prevents degeneration of the sampled gases which contributes to the equalization of the measurement conditions of the gases.

Other features and details of the present invention are fully disclosed in the following description of a preferred embodiment.

DETAILED DESCRIPTION OF A PREFERRED EMBODIMENT

Figure 5:
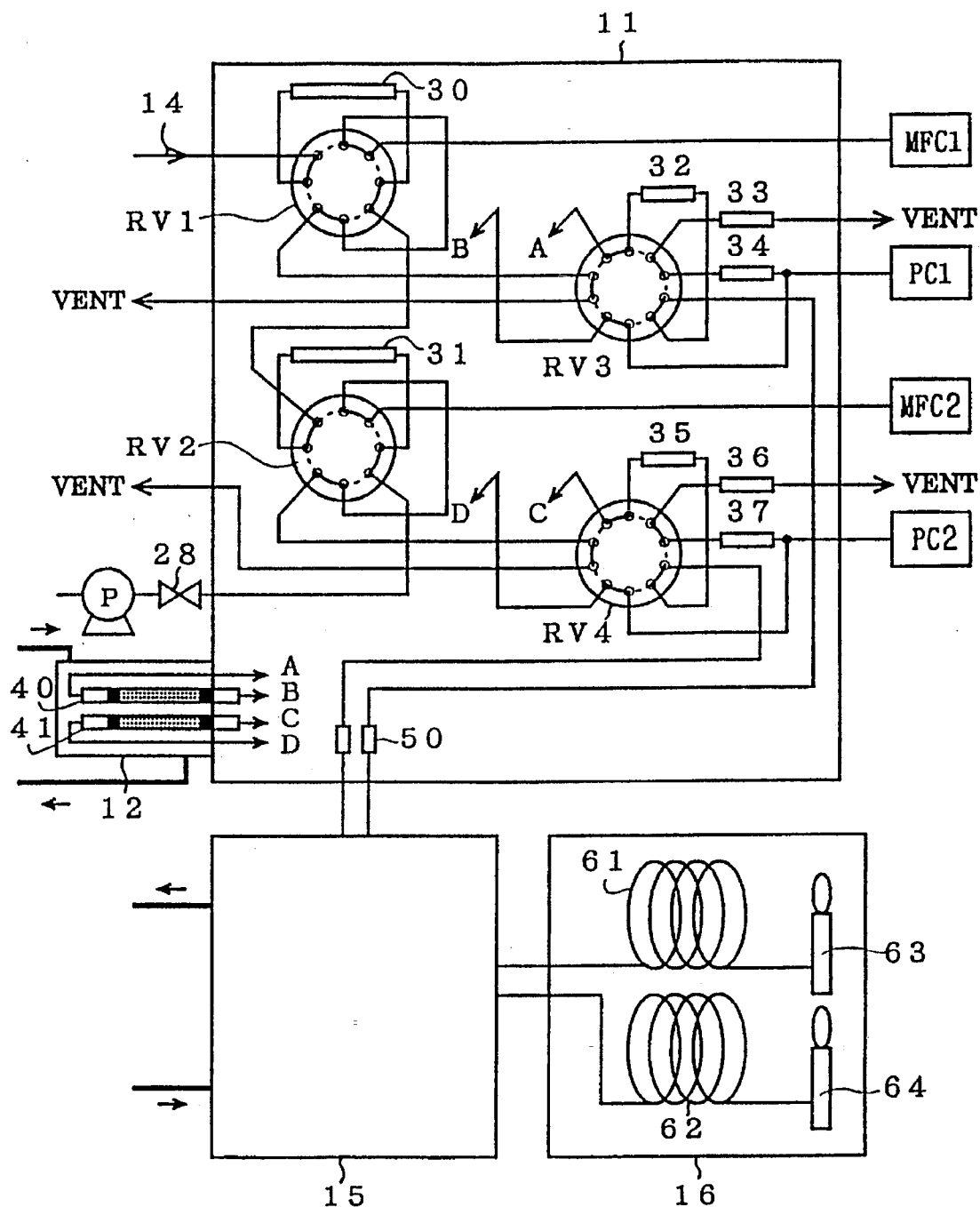
FIG. 5 is an illustrative diagram showing a detailed structure of a measuring section.
Figure 6:
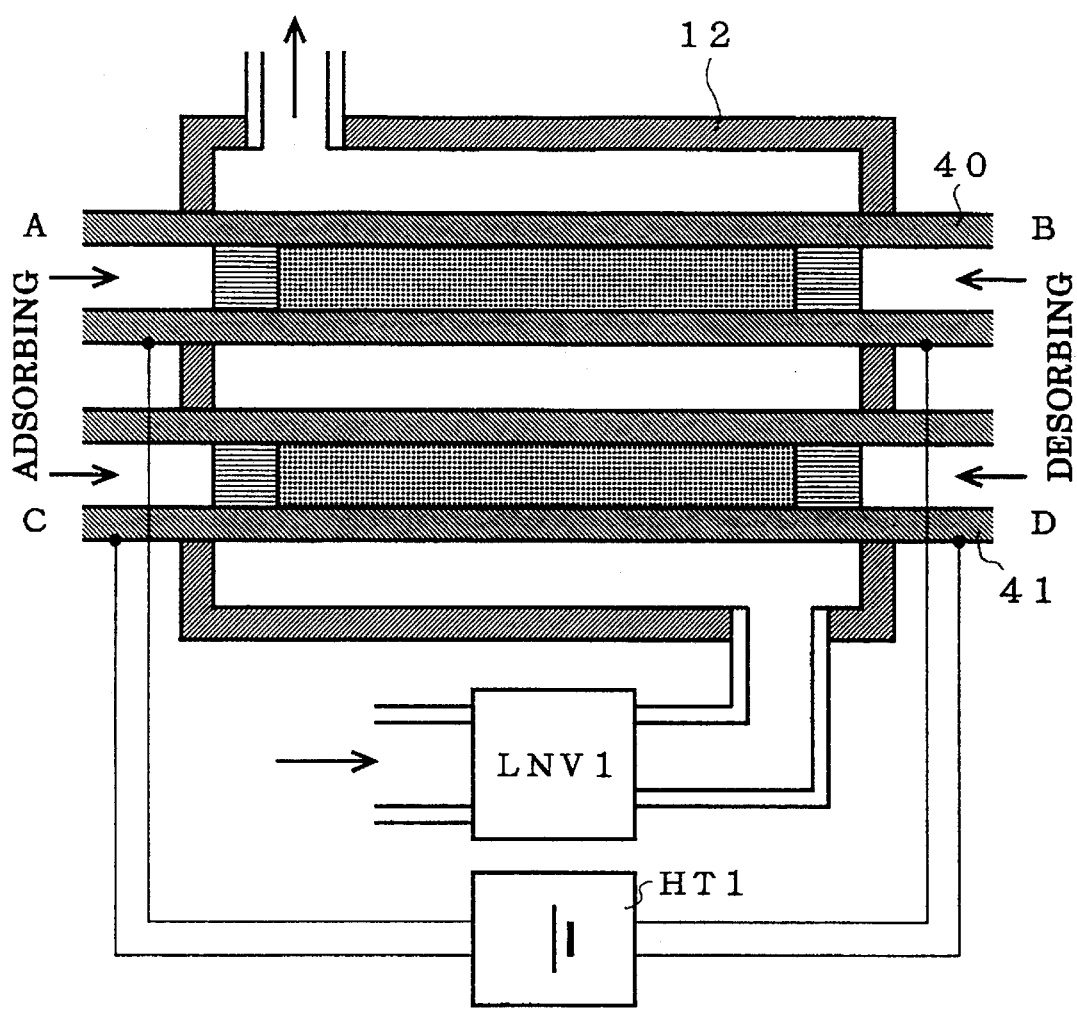
FIG. 6 is a cross-sectional view of a pre-concentrator.
Figure 7:
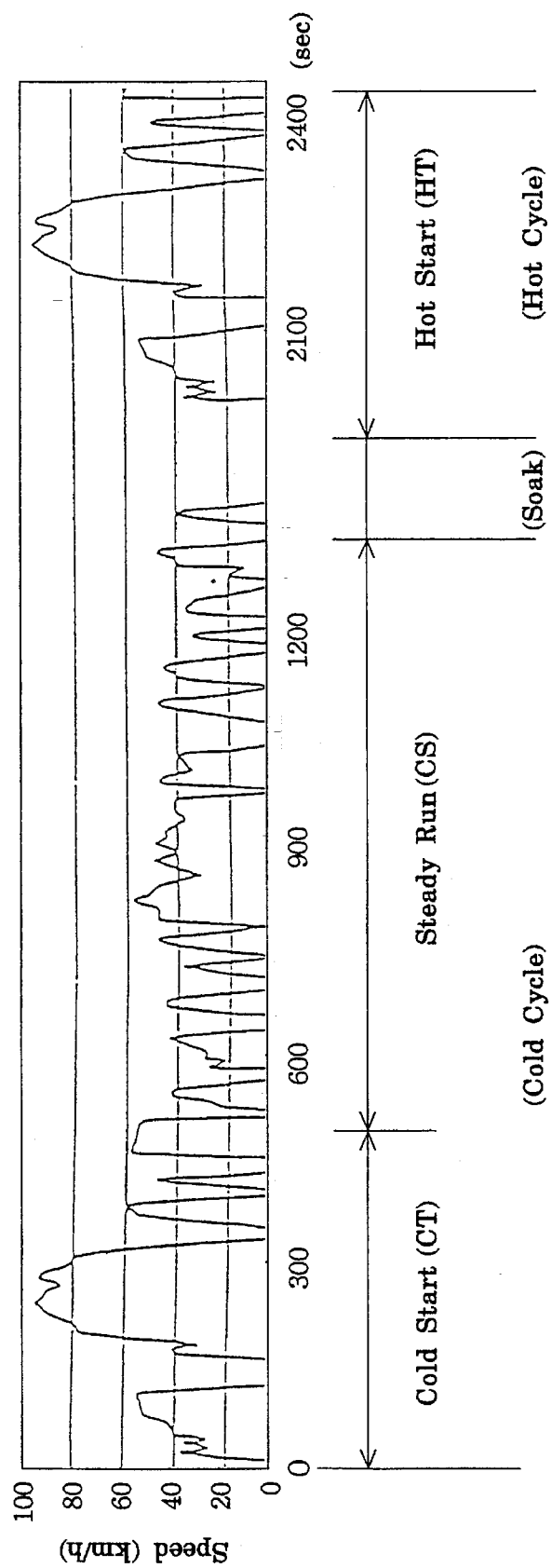
FIG. 7 is a graph of the run cycle pattern of the LA-4 regulation.

An automatic exhaust gas analyzer embodying the present invention is described by referring to FIGS. 1 through 7. The automatic analyzer of the present embodiment is made suitable to perform exhaust gas analysis according to the exhaust gas regulation LA-4 of the California State (as shown in FIG. 7) which is said to be the most stringent regulation in the world.

Figure 1:
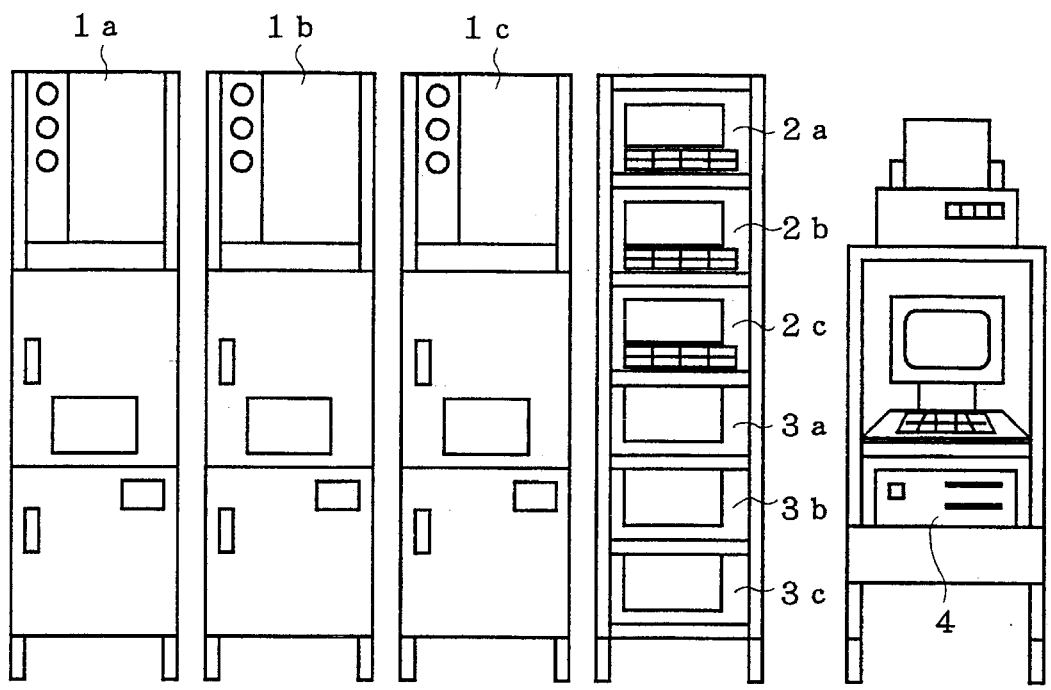
FIG. 1 is the front view of an automatic exhaust gas analyzer embodying the present invention.

As shown in FIG. 1, the exhaust gas analyzer of the present embodiment includes: three measuring sections $1a$, $1b$, $1c$; six signal analyzers $2a$, $2b$, $2c$, $3a$, $3b$, $3c$; and a data processor 4. The three measuring sections $1a$, $1b$, $1c$ are identical to one another and, as described later, each of the three measuring sections $1a$, $1b$, $1c$ includes four gas signal lines for independently measuring two kinds of gas in two ranges: i.e., a lower carbon number range between C2 to C6 and in a higher carbon number range between C6 to C12. Each of the six signal analyzers $2a$, $2b$, $2c$, $3a$, $3b$, $3c$ has two channels of analog signal input circuits, and the twelve analog signal input circuits respectively receive output signals from the three measuring sections 1a, 1b, 1c of the four gas signal lines. The signal analyzers 2a, 2b, 2c, 3a, 3b, 3c analyze the received signals and produce analysis data for the lower carbon-number range and the higher carbon-number range separately. A measuring section and two signal analyzers connected thereto correspond to an analyzing unit of the present invention. A personal computer is used as the data processor 4 in the present embodiment on which specially provided data processing programs are run to perform necessary data analysis according to the LA-4 regulation.

Figure 2:
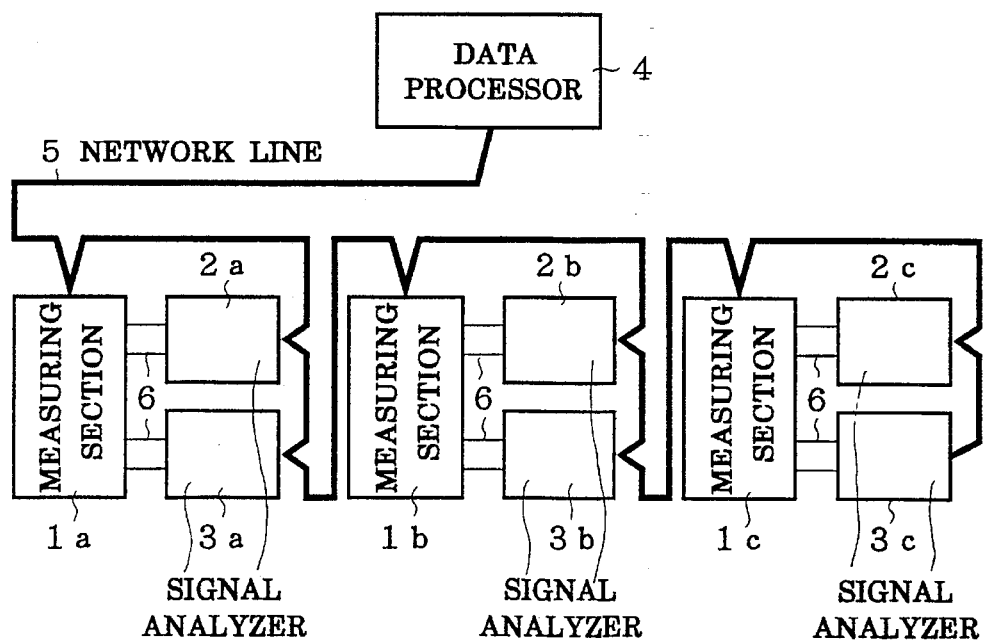
FIG. 2 is a block diagram of the electrical circuit of the embodiment.

The electrical connection of the measuring sections 1a, 1b, 1c, the signal analyzers 2a, 2b, 2c, 3a, 3b, 3c, and the data processor 4 is shown in FIG. 2. As described above, two signal analyzers are connected to each of the three measuring sections 1a, 1b, 1c with two analog signal lines 6. The three measuring sections 1a, 1b, 1c and the six signal analyzers 2a, 2b, 2c, 3a, 3b, 3c respectively have a terminal device for data communication, whereby they and the data processing section 4 are connected in cascade by a network line 5.

Figure 3:
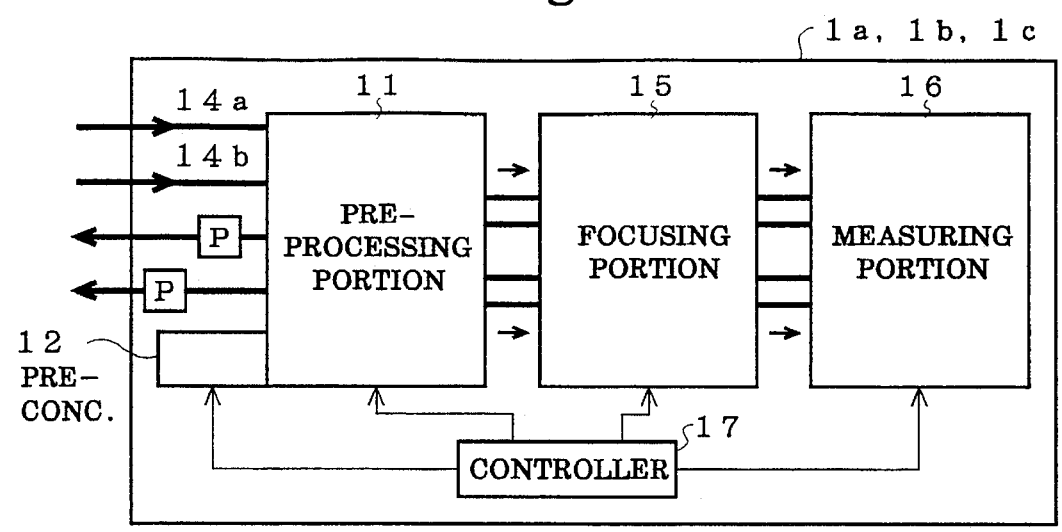
FIG. 3 is a block diagram showing an abstract structure of a measuring section.

As shown in FIG. 3, each of the measuring sections 1a, 1b, 1c includes: a pre-processing portion 11, a pre-concentrator 12, a focusing portion 15, a measuring portion 16 and a controller 17. The pre-processing portion 11 inhales two kinds of gas (exhaust gas and the background gas in the case of LA-14 test) separately through two inlets 14a and 14b. In the pre-processing portion 11, the inhaled gas is divided into two separate flows after it is metered (thus there are four separate gas flows in a pre-processing portion 11). Gas in one of the two flows is operated to include only components of C1 to C12 and gas in the other flow is operated to include only components of C1 to C6. The pre-concentrator 12 is used in the gas processing by the pre-processing portion 11. It concentrates the gas of each flow to increase the density of the hydrocarbon components of the gas to be measured. The focusing portion 15 is used to decrease the width and increase the height of the peaks of a chromatogram. A measuring portion 16 includes four columns (main columns) and four detectors. Each column separates components included in the sample gas flowing in the column and the corresponding detector detects the components. The controller 17 (which is provided for each of the three measuring sections 1a, 1b, 1c) controls the movement of two-position rotary valves, coolers and heaters included in the aforementioned portions.

The two gases inhaled by the pre-processing portion 11 are treated equally among the three measuring sections 1a, 1b, 1c, and the two gases are treated in parallel and simultaneously in each of the measuring sections 1a, 1b, 1c. Thus the treatment of a gas is detailed be referring to FIGS. 4 through 7.

(1) Pre-processing portion 11

As shown in FIG. 5, a first rotary valve RV1 and a second rotary valve RV2 are disposed between the inlet 14 and a pump P. The first and the second rotary valves RV1 and RV2 are both eight-port valves, and a sample loop 30 or 31 is disposed between two of the eight ports of each rotary valve RV1 or RV2. Sample gas introduced through the inlet into the gas chromatographic analyzer of the present embodiment is first metered by the sample loops 30 and 31 of the first and second rotary valves RV1 and RV2. The two volumes of the metered sample gas then flow through two lines provided in each of the measuring sections 1a, 1b, 1c independently. The line corresponding to the first rotary valve RV1 is then referred to as the first line and that corresponding to the second rotary valve RV2 is as the second line. Since a measuring section 1a, 1b or 1c admits two kinds of gas at the same time, there are four independent lines in a measuring section 1a, 1b or 1c. A third rotary valve RV3 and a fourth rotary valve RV4 are disposed in the first and second lines respectively within the pre-processing portion 11. The third and the fourth rotary valves RV3 and RV4 are both ten-port valves, and a pre-column 32 or 35, choke column 33 or 36, dummy column 34 or 37, mass flow controller MFC1 or MFC2, and a pressure controller PC1 or PC2 is connected to each of the third and the fourth rotary valves RV3 and RV4.

(2) Pre-concentrator 12

As shown in FIG. 5, the pre-concentrator 12 includes two columns 40 and 41 within which ordinary column material is contained. The two columns 40 and 41 are connected to the ports of the third and fourth rotary valves RV3 and RV4 respectively. As shown in FIG. 6, an insulated closed space is provided around the columns 40 and 41 in which liquid nitrogen ($LN_2$) is introduced through a valve $LNV_1$ to cool the columns 40 and 41 to about minus 170° C. The columns 40 and 41 are made of metal pipes and can be joule heated by the electric power from a power source HT1.

(3) Focusing portion 15

Figure 4:
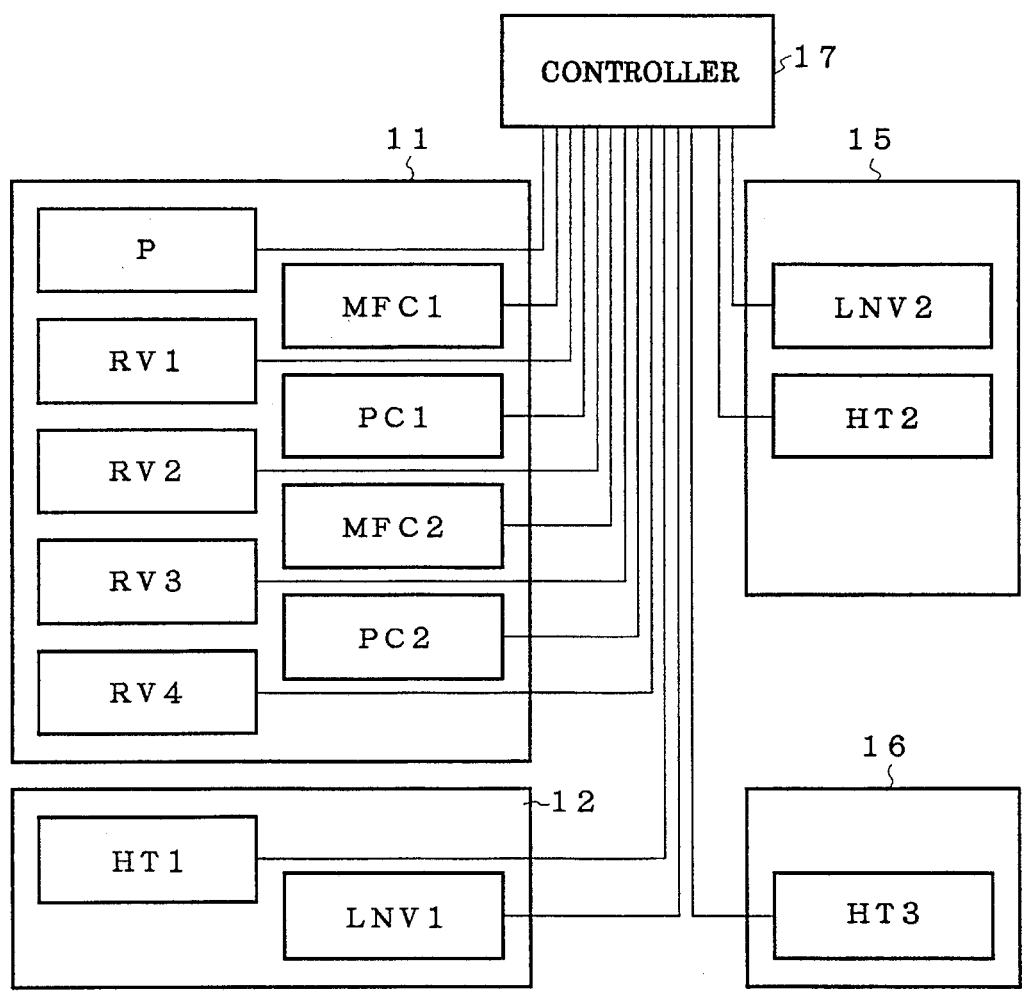
FIG. 4 is a block diagram showing the electrical circuit of a measuring section.

In a focusing portion 15, a focusing column (not shown) is provided for each of the first and second gas lines (thus four focusing columns in a measuring section). Similarly to the pre-concentrator 12, the focusing column can be cooled by introducing liquid nitrogen into the focusing portion 15 through a valve LNV2 (FIG. 4), and can be heated by a heater HT2 (FIG. 4).

(4) Measuring portion 16

A main column 61 or 62 and a detector 63 or 64 are provided for each of the first and second gas lines (thus four columns and four detectors in a measuring section). Though a capillary column is used as the main column 61 or 62 in the present embodiment, it is possible to use a packed column. A flame ionization detector (FID) is normally used as the detector 63 or 64, but any other detector can be used. The measuring portion 16 is provided with a heater HT3 for heating the whole portion from about 40° to 180° C.

(5) Controller 17

As shown in FIG. 4, the controller 17 is connected to the pump P, to the rotary valves RV1 through RV4, to the mass flow controllers MFC1 and MFC2, to the pressure controllers PC1 and PC2, to the liquid nitrogen valves LNV1 and LNV2 and to the heaters (or the power sources) HT1 through HT3, and controls them according to preset programs which are described above. The controller 17 can include a micro computer or, alternatively, can be made of sequence switches and relays.

The process of analyzing exhaust gas according to the LA-4 regulation using the automatic exhaust gas analyzer of the present embodiment is now described.

(1) Gas sampling

In the LA-4 regulation, a sample automobile runs according to a preset run pattern, as shown in FIG. 7, which includes:

a) A cold start stage (CT) which is the period until 505 sec from the very beginning (0 sec);

b) A steady run stage (CS) which is the period between 505 sec to 1372 sec; and c) A hot start stage (HT) which is the 505 sec period after the steady run stage (CS) and a 600 sec soaking period.

Exhaust gas of a sample automobile and the ambient air (background air) are sampled at each of the above stages. The exhaust gas is diluted ten times with the background gas. The gases are sampled using preset sampling bags, and then the two sampling bags are brought to one of the three measuring sections (say the measuring section 1a) and attached to the two inlets 14a and 14b respectively. Since the two gases are treated in the same way, the following description is made for the exhaust gas only.

(2) Metering

First, the position of the first and the second rotary valves RV1 and RV2 are set as shown by the solid lines of FIG. 5. The exhaust gas inhaled through the inlet 14a (or the background gas inhaled through the other inlet 14b) is exhaled by the pump P through: the first rotary valve RV1—the sample loop 30—the first rotary valve RV1—the second rotary valve RV2—the sample loop 31—the second rotary valve RV2—the valve 28.

When the exhaust gas is filled in both of the sample loops 30 and 31, the controller 17 rotates the two rotary valves RV1 and RV2 by 45° to set them in the position shown by the dotted lines of FIG. 5. Then the controller 17 drives the mass flow controllers MFC1 and MFC2 to supply carrier gas to the first and the second rotary valves RV1 and RV2, whereby the carrier gas flows from the mass flow controller MFC1 to the first rotary valve RV1—the sample loop 30—the first rotary valve RV1—the third rotary valve RV3, pressing the volume of the exhaust gas stored in the sample loop 30. The volume of the exhaust gas in the other sample loop 31 is also pressed by the carrier gas supplied by the mass flow controller MFC2 to the fourth rotary valve RV4.

(3) Pre-concentration

The third and the fourth rotary valves RV3 and RV4 are first placed at the position shown by the dotted lines of FIG. 5, whereby the volume of the exhaust gas from the first rotary valve RV1 is sent through the third rotary valve RV3 to the column 40 of the pre-concentrator 12. Before that, the valve LNV1 is opened by the controller 17 and the column 40 is cooled by liquid nitrogen $LN_2$. The volume of exhaust gas from the third rotary valve RV3 flows from the end A to the end B of the column 40, during which hydrocarbonic components of the exhaust gas are adsorbed on the surface of the cooled material in the column. After passing through the column 40 of the pre-concentrator 12, the exhaust gas (which is devoid of the analyzing object of hydrocarbonic components) returns to the third rotary valve RV3 and is released to the atmosphere (through the VENT in the left of FIG. 5). The above operations are just the same in the second gas line including the fourth rotary valve RV4 and the other column 41.

After supplying a preset volume of carrier gas from the mass flow controller MFC1, the controller 17 rotates the third rotary valve RV3 by 36° to the position shown by the solid lines. Then the controller 17 shuts the liquid nitrogen valve LNV1 of the pre-concentrator 12 and supplies electric current from the power source HT1 to the columns 40 and 41 to heat the columns 40 and 41. At the same time, the controller 17 drives the pressure controller PC1 to supply a preset pressure of carrier gas to the pre-concentrator 12 through the third rotary valve RV3. This time, contrary to the case before, the carrier gas flows from the end B to the end A of the column 40. By this operation, the components adsorbed on the surface of the material in the column 40 are desorbed therefrom. It is noted here that, since the temperature of the column 40 is set adequately high, the components are desorbed at high speed whereby the exhaust gas is pre-concentrated. The same applies to the second gas line including the fourth rotary valve RV4 and the other column 41.

(4) Separation

The exhaust gas pre-concentrated and returned to the third rotary valve RV3 flows through the pre-column 32, where the pre-concentrated exhaust gas is separated according to the carbon number, and the components leave the pre-column to the focusing portion 15 in the order of smaller carbon number. When the components C12 and less have passed the pre-column, the controller 17 rotates the third rotary valve RV3 by 36° to the position shown by the dotted lines. At this time, components of the larger carbon numbers (C13 and more) are in the pre-column or in the line before that. The carrier gas from the pressure controller PC1 flows through the third rotary valve RV3 to the pre-column 32 in the opposite direction, whereby the larger carbon number components (C13 and more) are pressed back and are released through the choke column 33 to the atmosphere (VENT). The choke column 33 is a dummy column having the same flow resistance as the main column 61 (described later).

The other volume of the exhaust gas pre-concentrated in the pre-concentrator 12 and brought back to the fourth rotary valve RV4 is similarly operated and separated as above, but the fourth rotary valve RV4 is rotated earlier than the third rotary valve RV3 to let components of smaller carbon numbers (C6 and less) flow to the focusing portion 15, arresting components of larger carbon numbers (C7 and more). The larger carbon number components are released through the pre-column 35 to the atmosphere. Thus, components of C1 to C12 are sent through the first gas line, and components of C1 to C6 are sent through the second gas line, to the focusing portion 15. The timing of the rotation of the third and the fourth rotary valves RV3 and RV4 are predetermined experimentally.

(5) Focusing

The pre-concentrated exhaust gas is again concentrated similarly to the way as done in the pre-concentrator 12. That is, in the first gas line for example, the liquid nitrogen valve LNV2 (FIG. 4) is opened and a column in the focusing portion 15 is cooled by liquid nitrogen. Then the concentrated exhaust gas flows through the column where the object components of the exhaust gas are adsorbed on the inner wall of the column (capillary column). When the column is heated by the heater HT2 (FIG. 4), the adsorbed components are desorbed at high speed. The same applies to the second gas line.

(6) Measurement

The exhaust gas from the focusing portion 15 in the first gas line including only C12 and less components flows through the main column 61, where all components are separated. The detector 63 mainly detects the later separated components, that are C6 to C12 components. In the second gas line, the exhaust gas includes only C6 and less components, whereby the components separated by the main column 62 are detected from the beginning by the detector 64 at high precision. Thus the smaller carbon number components of C1 to C6 are detected by the detector 64 of the second gas line, and the larger carbon number components of C6 to C12 are detected by the detector 63 of the first gas line, respectively at high precision.

The signals generated by the detectors 63 and 64 are sent via the analog signal line 6 to the signal analyzer 2a, where the concentration values of the hydrocarbonic components from C1 to C12 are determined respectively. In the present embodiment, the detector 63, 64 and the signal analyzers 2a, 2b, 2c, 3a, 3b, 3c combined correspond to the gas-chromatic detector of the present invention.

A session of measurement as described above in a measuring section normally takes about one hour, while the duration of a cycle of the LA-4 run pattern is about 40 minutes within which three sampling should be done, as shown in FIG. 7. Thus in the automatic exhaust gas analyzer of the present embodiment, the exhaust gas and the background gas in the second time sampling are immediately delivered to the second measuring section 1b, and the exhaust gas and the background gas in the third time sampling are immediately delivered to the third measuring section 1c. This immediate delivery prevents degeneration of the sampled exhaust gas and enables analysis of raw samples which helps to equalize the analyzing conditions and assures meaningful data comparison.

The concentration data of components of the sample gas produced by the six analyzing sections 2a, 2b, 2c, 3a, 3b, 3c is sent via the network line 5 to the data processor 4. After gathering the data, the data processor 4 performs a preset data processing on the data to determine various component parameters of the exhaust gas according to the LA-4 regulation. The result data thus obtained is displayed on a screen or is printed out.

When a cycle of LA-4 test is performed, the conditions of the three measuring sections 1a, 1b and 1c should be the same. When, in the automatic exhaust gas analyzer of the present embodiment, the operator sets various measuring conditions on one of the three measuring sections (say, on the measuring section 1a), the data of the measuring conditions is transmitted through the network line 5 to the other two measuring sections 1b and 1c, and the measuring conditions of the other two measuring sections 1b and 1c are automatically set for the same.

In the above description, the LA-4 regulation is taken as an example only and the automatic exhaust gas analyzer of the present embodiment can be used in any other case where several kinds of gas are sampled with short time intervals and the sampled gas has a tendency to degenerate.

What is claimed is:

1. An automatic exhaust gas analyzer for analyzing both an exhaust gas of an internal combustion engine and a background gas simultaneously, the analyzer comprising:

a) a plurality of analyzing units;

b) two independent gas lines provided in each of the plurality of analyzing units for analyzing the exhaust gas and the background gas;

c) a gas-chromatographic column provided in each of the independent gas lines;

d) a gas-chromatographic detector connected with the column in each of the independent gas lines;

e) signal communication network means for interconnecting and conveying signals between each of the gas-chromatographic detectors;

f) analysis control means for sampling the exhaust gas and the background gas at the same time, the analysis control means supplies the sampled exhaust gas and the sampled background gas to the two independent gas lines respectively and for analyzing the exhaust gas and the background gas independently using the gas-chromatographic columns and the gas-chromatographic detectors under same analyzing conditions set by the signal communication network means; and g) a separator provided in each of the two gas lines for separating a first gas including hydrocarbon components of C12 and less and a second gas including hydrocarbon components of C6 and less respectively from the exhaust gas and the background gas.

2. The automatic exhaust gas analyzer according to claim 1, wherein each of the plurality of analyzing units further comprises:

f) a signal analyzer for analyzing a signal from the gas-chromatographic detectors comprised in the analyzing unit and for producing measurement data; and g) a data processor for processing the measurement data and for producing predetermined parameters of the exhaust gas.

3. The automatic exhaust gas analyzer according to claim 2, wherein the signal communication network means conveys signals from a first of the plurality of analyzing units which produces a predetermined parameter to the others of the plurality of analyzing units.

4. The automatic exhaust gas analyzer according to claim 3, wherein a pre-concentrator is provided in each of the two gas lines for concentrating the exhaust gas and the background gas using liquid nitrogen.

5. The automatic exhaust gas analyzer according to claim 1, wherein a gas-chromatographic column and a gas-chromatographic detector are provided for the first gas and the second gas respectively after the separator in each of the gas lines.

* * * * *